(12) United States Patent
Kageyama et al.

(10) Patent No.: US 10,975,026 B2
(45) Date of Patent: Apr. 13, 2021

(54) METHOD FOR PRODUCING POLYTHIOL COMPOUND, METHOD FOR PRODUCING CURABLE COMPOSITION, AND METHOD FOR PRODUCING CURED PRODUCT

(71) Applicant: HOYA LENS THAILAND LTD., Pathumthani (TH)

(72) Inventors: Yukio Kageyama, Tokyo (JP); Masahisa Kousaka, Tokyo (JP); Akinori Yamamoto, Tokyo (JP)

(73) Assignee: HOYA LENS THAILAND LTD., Pathumthani (TH)

( * ) Notice: Subject to any disclaimer, the term of this patent is extended or adjusted under 35 U.S.C. 154(b) by 0 days.

(21) Appl. No.: 16/171,476

(22) Filed: Oct. 26, 2018

(65) Prior Publication Data
US 2019/0062270 A1 Feb. 28, 2019

Related U.S. Application Data

(63) Continuation of application No. PCT/JP2016/069443, filed on Jun. 30, 2016.

(51) Int. Cl.
*C07C 319/14* (2006.01)
*C07C 319/20* (2006.01)
(Continued)

(52) U.S. Cl.
CPC .......... *C07C 319/14* (2013.01); *C07C 319/20* (2013.01); *C07C 335/32* (2013.01);
(Continued)

(58) Field of Classification Search
None
See application file for complete search history.

(56) References Cited

U.S. PATENT DOCUMENTS

| 5,087,758 A | 2/1992 | Kanemura et al. |
| 5,191,055 A | 3/1993 | Kanemura et al. |

(Continued)

FOREIGN PATENT DOCUMENTS

| CN | 104271629 A | 1/2015 |
| CN | 104321306 A | 1/2015 |

(Continued)

OTHER PUBLICATIONS

Sep. 20, 2016 International Search Report issued in International Patent Application No. PCT/JP2016/069443.
(Continued)

*Primary Examiner* — Tae H Yoon

(74) *Attorney, Agent, or Firm* — Oliff PLC

(57) ABSTRACT

The method for producing a polythiol compound includes reacting 2-mercaptoethanol having a water content of 3000 ppm or less on a mass basis, with epihalohydrin to obtain a halide represented by the formula (1), wherein X represents a halogen atom; and obtaining at least one polythiol compound selected from the group consisting of a polythiol compound represented by the formula (4), a polythiol compound represented by the formula (5), a polythiol compound represented by the formula (6), and a polythiol compound represented by the formula (7).

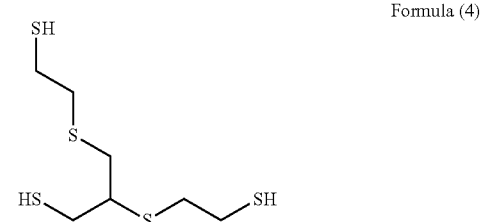

Formula (4)

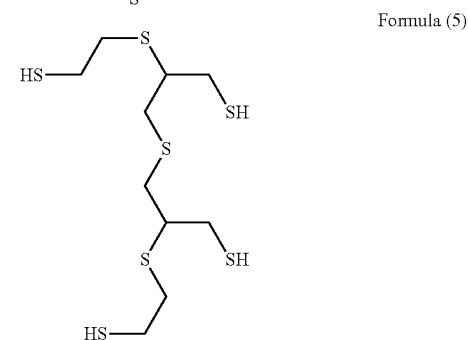

Formula (5)

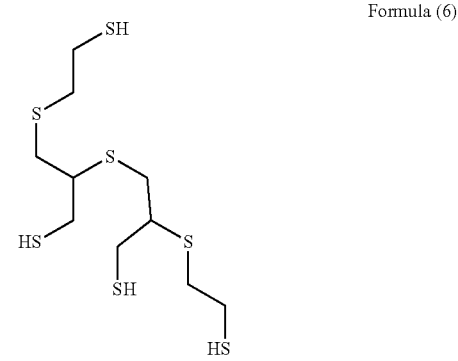

Formula (6)

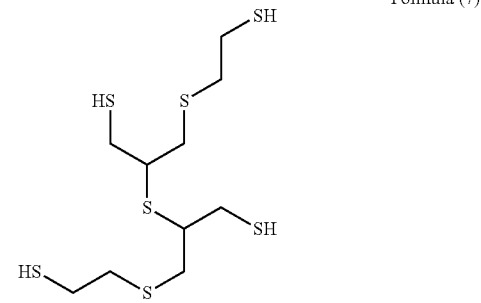

Formula (7)

16 Claims, No Drawings

(51) Int. Cl.
  *C07C 335/32* (2006.01)
  *G02B 1/04* (2006.01)
  *C08G 18/24* (2006.01)
  *C08G 18/76* (2006.01)
  *C08G 18/38* (2006.01)

(52) U.S. Cl.
  CPC ....... *C08G 18/246* (2013.01); *C08G 18/3876* (2013.01); *C08G 18/7642* (2013.01); *G02B 1/04* (2013.01); *G02B 1/041* (2013.01)

(56) References Cited

U.S. PATENT DOCUMENTS

| | | | |
|---|---|---|---|
| 5,608,115 | A | 3/1997 | Okazaki et al. |
| 5,837,797 | A | 11/1998 | Okazaki et al. |
| 6,100,362 | A | 8/2000 | Okazaki et al. |
| 10,611,726 | B2 * | 4/2020 | Kageyama ............... G02B 3/00 |
| 2009/0082544 | A1 | 3/2009 | Kuma et al. |
| 2010/0010192 | A1 | 1/2010 | Kawaguchi et al. |
| 2010/0280213 | A1 | 11/2010 | Kuma et al. |
| 2011/0176220 | A1 | 7/2011 | Kuma et al. |
| 2015/0018507 | A1 * | 1/2015 | Jang ...................... C07C 319/14 528/77 |
| 2015/0126781 | A1 | 5/2015 | Kawaguchi et al. |
| 2015/0133692 | A1 | 5/2015 | Kawaguchi et al. |
| 2016/0017085 | A1 | 1/2016 | Kawaguchi et al. |
| 2016/0024242 | A1 | 1/2016 | Kawaguchi et al. |

FOREIGN PATENT DOCUMENTS

| | | |
|---|---|---|
| CN | 104321307 A | 1/2015 |
| IN | 2342 DE2004 A | 8/2006 |
| JP | H02-270859 A | 11/1990 |
| JP | H07-252207 A | 10/1995 |
| JP | 2006-162926 A | 6/2006 |
| JP | 5319037 B1 | 10/2013 |
| KR | 10-2012-0058635 A | 6/2012 |
| WO | 2007/129449 A1 | 11/2007 |
| WO | 2008/047626 A1 | 4/2008 |
| WO | 2014/027428 A1 | 2/2014 |

OTHER PUBLICATIONS

Jan. 1, 2019 International Preliminary Report on Patentability issued in International Patent Application No. PCT/JP2016/069443.
Nov. 1, 2019 Office Action issued in Chinese Patent Application No. 201680083976.7.
Jan. 8, 2020 Extended Search Report issued in European Patent Application No. 16907292.3.

* cited by examiner

METHOD FOR PRODUCING POLYTHIOL COMPOUND, METHOD FOR PRODUCING CURABLE COMPOSITION, AND METHOD FOR PRODUCING CURED PRODUCT

CROSS-REFERENCE TO RELATED APPLICATIONS

This application is a Continuation of PCT International Application No. PCT/JP2016/069443 filed on Jun. 30, 2016, which was published under PCT Article 21(2) in Japanese. The above application is hereby expressly incorporated by reference, in its entirety, into the present application.

TECHNICAL FIELD

The present disclosure relates to a method for producing a polythiol compound, a method for producing a curable composition, and a method for producing a cured product.

BACKGROUND ART

A polythiol compound is widely used as a synthetic raw material for obtaining various resins. For example, a polythiourethane-based resin can be synthesized by a curing reaction between a polythiol compound and a polyiso(thio)cyanate compound (see, for example, paragraph 0004 of Patent Literature 1).

Patent Literature 1: JP 5319037 B2

SUMMARY

As described in Patent Literature 1, a polythiol compound can be produced by using 2-mercaptoethanol as a starting material. However, as a result of intensive investigations on a method for producing a polythiol compound by the present inventors, it has become clear that a conventional method for synthesizing a polythiol compound has the following problems (1) and (2):

(1) further improvement in yield constant is required for improvement in productivity; and (2) reduction in coloration of the polythiol compound to be produced is required.

One aspect of the present disclosure provides for a method for producing a polythiol compound capable of producing a polythiol compound with reduced coloration in high yield constant.

The present inventors got the following new finding conventionally unknown, during the repetition of intensive studies: moisture contained in 2-mercaptoethanol as a starting material for a polythiol compound largely affects reductions in the coloration and yield constant of the polythiol compound. As a result of further intensive studies based on this finding, the present inventors have found a method for producing a polythiol compound according to one aspect of the present disclosure.

That is, one aspect of the present disclosure relates to a method for producing a polythiol compound, the method including the following steps:

step 1 of reacting 2-mercaptoethanol having a water content of 3000 ppm or less on a mass basis (hereinafter also simply referred to as "water content"), with epihalohydrin to obtain a halide represented by the formula (1),

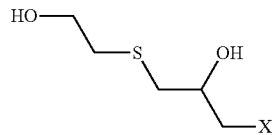

Formula (1)

wherein X represents a halogen atom; step 2 of reacting the halide represented by the formula (1) with an alkali metal compound selected from the group consisting of an alkali metal sulfide and an alkali metal hydroxide to obtain a polyol compound selected from the group consisting of a polyol compound represented by the formula (2) and a polyol compound represented by the formula (3),

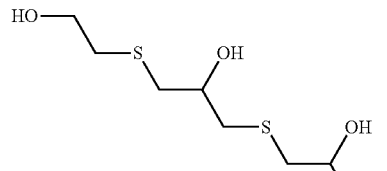

Formula (2)

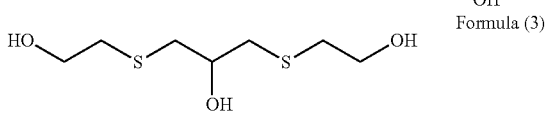

Formula (3)

step 3 of reacting the polyol compound with thiourea in the presence of an acid to obtain an isothiuronium salt;

step 4 of hydrolyzing the isothiuronium salt in the presence of a base to obtain a polythiol salt; and step 5 of converting the polythiol salt into a polythiol by an acid to obtain at least one polythiol compound selected from the group consisting of a polythiol compound represented by the formula (4), a polythiol compound represented by the formula (5), a polythiol compound represented by the formula (6), and a polythiol compound represented by the formula (7),

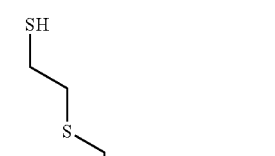

Formula (4)

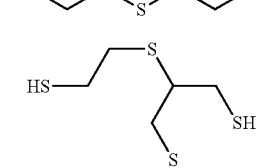

Formula (5)

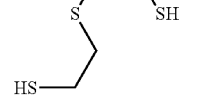

Formula (6)

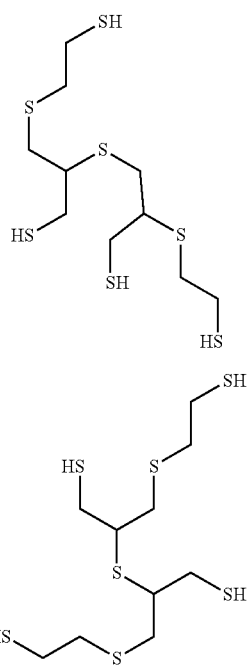

Formula (7)

One aspect of the present disclosure makes it possible to reduce the coloration of a polythiol compound useful as a synthesis raw material for various resins and to produce the polythiol compound in high yield constant.

DESCRIPTION OF EMBODIMENTS

Method for Producing Polythiol Compound

Hereinafter, a method for producing a polythiol compound according to one aspect of the present disclosure will be described in more detail.
<Step 1>
In step 1, 2-mercaptoethanol:

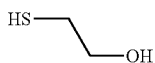

and epihalohydrin:

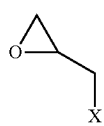

are reacted with each other. By step 1, a halide represented by the formula (1) can be obtained.

Formula (1)

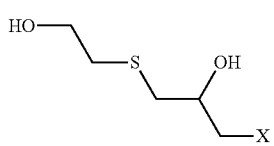

That is, in step 1, the halide represented by the formula (1) can be obtained by the following reaction scheme example 1.

Reaction Scheme Example 1

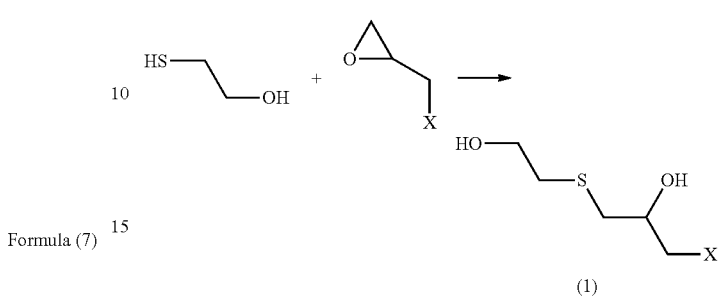

(1)

In the above epihalohydrin and formula (1), X represents a halogen atom. The halogen atom is, for example, a fluorine atom, a chlorine atom, a bromine atom, and an iodine atom. For example, by using epichlorohydrin (X=chlorine atom) as epihalohydrin in step 1, a halide can be obtained, in which X in the formula (1) is a chlorine atom. By using epibromohydrin (X=bromine atom) as epihalohydrin in step 1, a halide can be obtained, in which X in the formula (1) is a bromine atom.

In step 1, 2-mercaptoethanol having a water content of 3000 ppm or less on a mass basis is used as 2-mercaptoethanol. This makes it possible to improve the yield constant of the polythiol compound and to provide the polythiol compound with reduced coloration. From these viewpoints, the water content of 2-mercaptoethanol may be 2,800 ppm or less, 2,500 ppm or less, 2,300 ppm or less, 2,000 ppm or less, 1,800 ppm or less, 1500 ppm or less, 1300 ppm or less, or 1000 ppm or less. The water content of 2-mercaptoethanol can be, for example, 300 ppm or more or 500 ppm or more, but, in an embodiment, the water content is preferably as low as possible for improving yield constant and reducing coloration, whereby the water content may be lower than the lower limit exemplified above. The present inventors merely estimate the following: the hydrolysis of epihalohydrin caused by moisture in 2-mercaptoethanol causes reductions in the coloration and yield constant of the final polythiol compound. On the contrary, the present inventors consider that the ability to suppress the hydrolysis of epihalohydrin by using 2-mercaptoethanol having a low water content of 3000 ppm or less contributes to the ability to produce a polythiol compound with reduced coloration in high yield constant. However, the above is estimated, and does not limit the present disclosure at all.

The water content of 2-mercaptoethanol in the present disclosure and the present specification is a value measured by a Karl Fischer method using a water vaporizer under an environment of a temperature of 20 to 25° C. and an absolute humidity of 0.8 to 1.2 g/m³. The water content measurement provided by the Karl Fischer method may be carried out by a coulometric titration method or a volume titration method.

As a method for reducing the water content of 2-mercaptoethanol, for example, one or two or more of methods such as purification provided by distillation, dehydration using an inorganic salt anhydride such as magnesium sulfate or sodium sulfate, and dehydration using a molecular sieve can be used in combination. Thus, 2-mercaptoethanol having a water content of 3000 ppm or less can be obtained.

The reaction between 2-mercaptoethanol and epihalohydrin in step 1 may be carried out in the presence of a catalyst. As the catalyst, various known catalysts can be used, and a tertiary amine can be used. The tertiary amine may be a tertiary alkyl amine. Specific examples of the tertiary amine include trimethylamine, triethylamine, tripropylamine, tributylamine, N,N-dimethylcyclohexylamine, and N,N-dicyclohexylmethylamine.

A reaction temperature in step 1 and a reaction temperature in step 2 to be described later may be, for example, about 0 to 60° C. A reaction time in step 1 may be, for example, about 0.5 to 10 hours. The "reaction temperature" in the present disclosure and the present specification means the solution temperature of a reaction solution, and is also described as an "internal temperature".

In one aspect, step 1 can be carried out, for example, as follows. First, 2-mercaptoethanol is mixed to obtain a mixed solution. Here, a catalyst, for example, a tertiary amine may be mixed. If necessary, a solvent (for example, alcohol or the like) may be added. Thereafter, epihalohydrin is added to the mixed solution. Epihalohydrin may be added dropwise to the mixed solution. A dropping time may be, for example, about 0.1 to 5 hours, but it is not particularly limited. During the dropwise addition, the mixed solution may be stirred as necessary. Epihalohydrin can be reacted with 2-mercaptoethanol at a ratio of, for example, 0.5 to 3.0 mol, 0.7 to 2.0 mol, or 0.9 to 1.1 mol based on 1.0 mol of 2-mercaptoethanol. The tertiary amine can be used in an amount of, for example, about 0.005 to 0.1 mol based on 1.0 mol of epihalohydrin. After the addition of epihalohydrin, the mixed solution may be aged for about 0.5 to 10 hours as necessary. During the aging, the mixed solution may be left to stand, or may be stirred. In step 1, one or two or more tertiary amines can be used as the tertiary amine. When two or more tertiary amines are used, the amount of the tertiary amines shall be the total content of the two or more tertiary amines. In the present disclosure and the present specification, unless otherwise specified, components which may have different structures may be used singly, or two or more thereof may be used. The content of the two or more components to be used means the total content of the two or more components.

<Step 2>

Next, step 2 will be described.

Step 2 is step of reacting the halide obtained in step 1 and represented by the formula (1) with an alkali metal compound selected from the group consisting of an alkali metal sulfide and an alkali metal hydroxide to obtain a polyol compound selected from the group consisting of a polyol compound represented by the formula (2) and a polyol compound represented by the formula (3).

Formula (2)

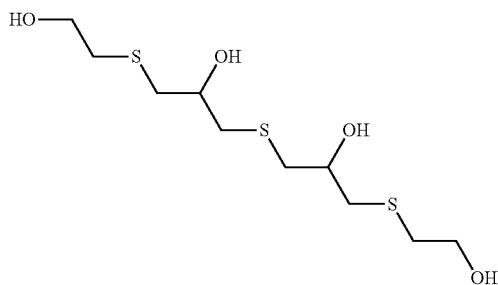

Formula (3)

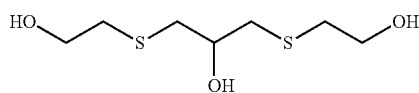

For example, when sodium sulfide is used as an example of the alkali metal compound, in step 2, the polyol compound represented by the formula (2) can be obtained by the following reaction scheme example 2. Numerical values described in the following reaction scheme example are based on a molar basis.

Reaction Scheme Example 2

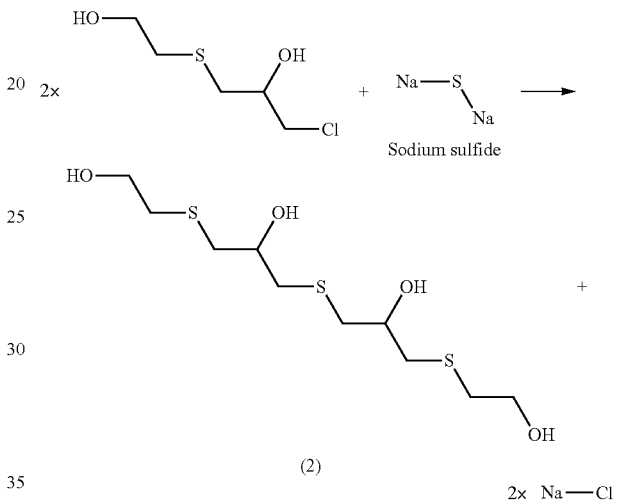

When sodium hydroxide is used as an example of the alkali metal compound, in step 2, the polyol compound represented by the formula (3) can be obtained by the following reaction scheme example 3.

Reaction Scheme Example 3

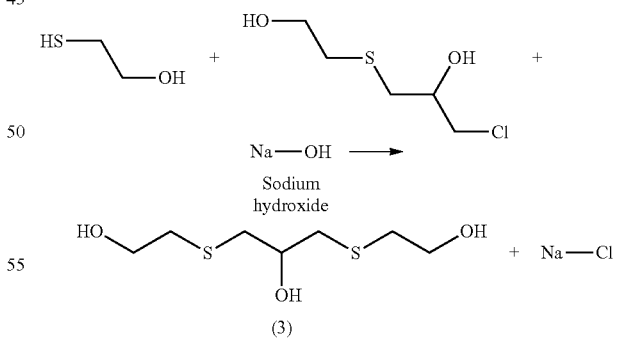

After the reaction of step 1, a reaction solution containing the intended product obtained by the reaction (the halide represented by the formula (1) in step 1) may be used as it is in the next step (step 2). The reaction solution after the intended product is isolated by purifying the reaction solution after the reaction of step 1 by a known method, or the concentration of the reaction solution is increased can also be used in the next step. The reaction solution after the reaction of step 1 can also be diluted with a solvent (for example, toluene or the like), and used in the next step. The above points are also the same after the reactions of steps 2 to 4. In an aspect using an alkali metal hydroxide as the alkali metal compound, as exemplified in the reaction scheme example 3, 2-mercaptoethanol is required to obtain the polyol compound represented by the formula (3). This 2-mercaptoethanol may be 2-mercaptoethanol which remains unreacted after the reaction of step 1, or may be added for step 2. In step 2, the amount of 2-mercaptoethanol used to obtain the polyol compound represented by the formula (3) may be, for example, 0.5 to 3.0 mol, 0.7 to 2.0 mol, or 0.9 to 1.1 mol based on 1.0 mol of the halide represented by the formula (1). When 2-mercaptoethanol is newly added to the reaction solution for step 2, the water content of 2-mercaptoethanol to be added may be 3000 ppm or less, or may be in the range described above in relation to step 1.

In the above reaction scheme examples 2 and 3, an example in which the alkali metal atom contained in the alkali metal compound selected from the group consisting of alkali metal sulfide and alkali metal hydroxide is sodium atom is shown. However, the alkali metal atom contained in the alkali metal compound may be another alkali metal atom such as a lithium atom or a potassium atom. In the reaction scheme example 2, the alkali metal compound is used at a ratio of, for example, 0.2 to 2.0 mol, 0.3 to 1.2 mol, or 0.4 to 0.6 mol based on 1.0 mol of the halide represented by the formula (1). In the reaction scheme example 3, the alkali metal compound is used at a ratio of, for example, 0.5 to 3.0 mol, 0.7 to 2.0 mol, or 0.9 to 1.1 mol, whereby the alkali metal compound can be reacted with the halide represented by the formula (1). The alkali metal compound may be in the form of a hydrate. The amount of the hydrate means an amount containing hydrated water. The alkali metal compound may be used as it is for the reaction of step 2, or may be used in the form of a solution such as an aqueous solution. In one aspect, the solution of the alkali metal compound can be added dropwise to a reaction solution containing the halide represented by the formula (1). A dropping time may be, for example, about 0.1 to 5 hours, but it is not particularly limited. During the dropwise addition, the reaction solution may be stirred as necessary. Such a reaction solution may be aged for about 0.5 to 10 hours as necessary after the addition of the alkali metal compound. During the aging, the reaction solution may be left to stand, or may be stirred.

<Step 3>

Next, step 3 will be described.

Step 3 is a step of reacting the polyol compound obtained in Step 2 with thiourea in the presence of an acid to obtain an isothiuronium salt. The "isothiuronium salt" is a quaternary salt of isothiourea. When hydrochloric acid is used as an example of the acid, for example, and the polyol compound represented by the formula (2) is reacted with thiourea in the presence of an acid, an isothiuronium salt shown in the following reaction scheme example 4 can be obtained. In Reaction Scheme Example 4, the isothiuronium salt having the skeleton of the polythiol compound (5) is shown, but in this reaction, the isothiuronium salt having the skeleton of the polythiol compound (5) and the skeleton of the polythiol compound (6) At least one isothiuronium salt selected from the group consisting of an isothiuronium salt and an isothiuronium salt having a skeleton of the polythiol compound (7) can be obtained. When the rearrangement reaction occurs, two or three of the isothiuronium salts can be obtained Respectively.

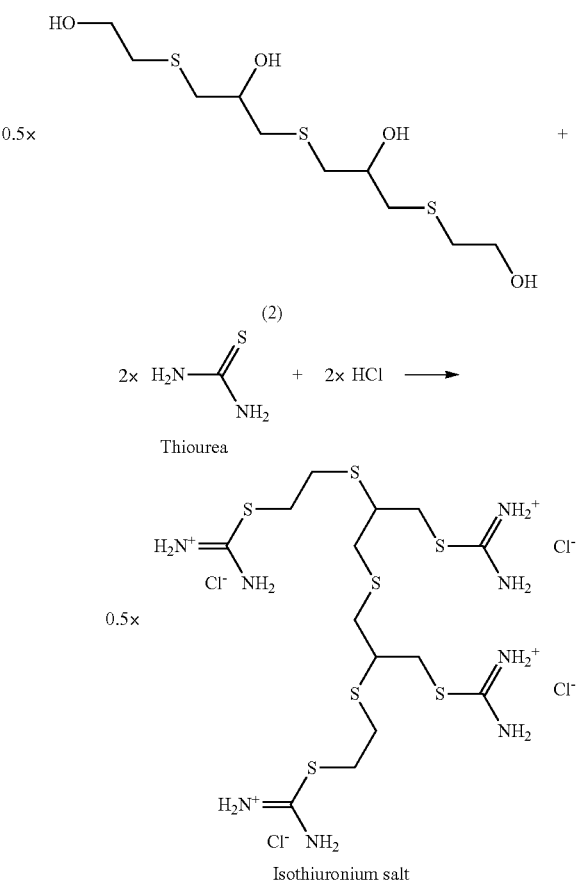

Reaction Scheme Example 4

For example, when the polyol compound represented by the formula (3) is reacted with thiourea in the presence of an acid, an isothiuronium salt having the skeleton of a polythiol compound (4) shown in the following reaction scheme example 5 can be obtained.

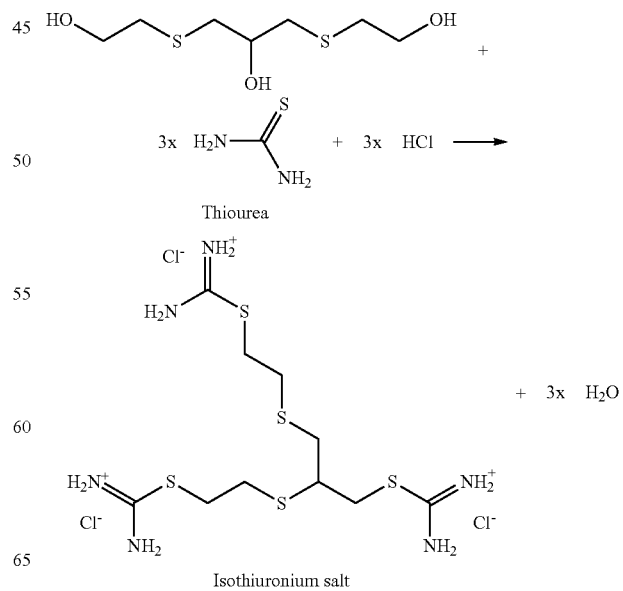

Reaction Scheme Example 5

In the above reaction scheme examples 4 and 5, examples using hydrogen chloride (HCl) as an acid are shown, but the acid used in step 3 is not limited to hydrogen chloride, and various inorganic acids and organic acids can be used. Examples of the inorganic acid include hydrogen chloride and sulfuric acid, and examples of the organic acids include formic acid. The form of addition of the acid is not limited, but the acid can be added, for example, as an aqueous solution. The concentration of the acid in the aqueous solution is not particularly limited, but it may be, for example, about 10 to 80% by mass. In step 3, the acid may be used at a ratio of, for example, 2.0 to 12.0 mol, or 3.0 to 8.0 mol based on 1.0 mol of the polyol compound (in the reaction solution containing two or more polyol compounds, the total amount thereof is 1.0 mol). Thiourea may be used at a ratio of, for example, 3.0 to 6.0 mol, or 4.5 to 5.5 mol in the reaction scheme example 4, and for example, 2.0 to 5.0 mol, or 3.5 to 4.5 mol in the reaction scheme example 5. In step 3, a reaction temperature may be, for example, from 40° C. to a reflux temperature, or may be about 90 to 120° C., and a reaction time may be, for example, from about 1 to 24 hours.

<Step 4>

Next, step 4 will be described.

Step 4 is step of hydrolyzing the isothiuronium salt obtained in step 3 in the presence of a base to obtain a polythiol salt. The polythiol salt obtained here is a salt having a structure in which a hydrogen atom of at least one thiol group of three or four thiol groups (—SH) present in one molecule of the polythiol compound represented by the formula (4), the formula (5), the formula (6), or the formula (7) is substituted. In step 4, two or more polythiol salts having different structures can also be obtained. The polythiol salt may be a polythiol alkali metal salt or a polythiol ammonium salt. The type of the salt can be adjusted by the type of the base used for hydrolysis. As an example, an aspect of obtaining an alkali metal salt as the polythiol salt will be described below.

The polythiol alkali metal salt has a structure in which the isothiuronium salt obtained in step 3 is hydrolyzed, as a result of which an alkali metal salt of a thiol group (—SM; M represents an alkali metal atom) is introduced into a molecular end. For example, a polythiol alkali metal salt (sodium salt) shown in the following reaction scheme example 6 can be obtained by hydrolyzing the isothiuronium salt having the skeleton of the polythiol compound (5) using sodium hydroxide as a base.

Reaction Scheme Example 6

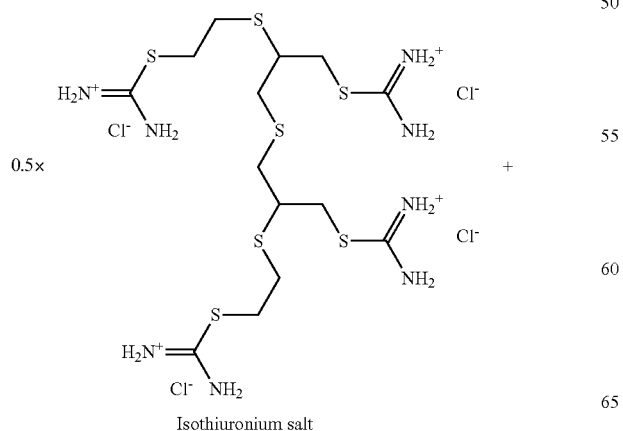

Isothiuronium salt

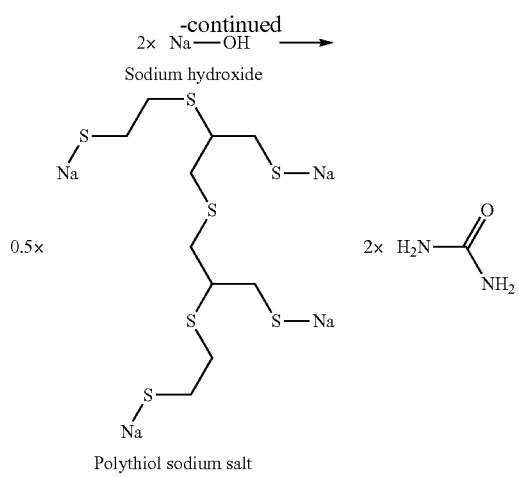

Polythiol sodium salt

A polythiol alkali metal salt (sodium salt) shown in the following reaction scheme example 7 can be obtained by hydrolyzing the isothiuronium salt having the skeleton of the polythiol compound (4) using sodium hydroxide as a base.

Reaction Scheme Example 7

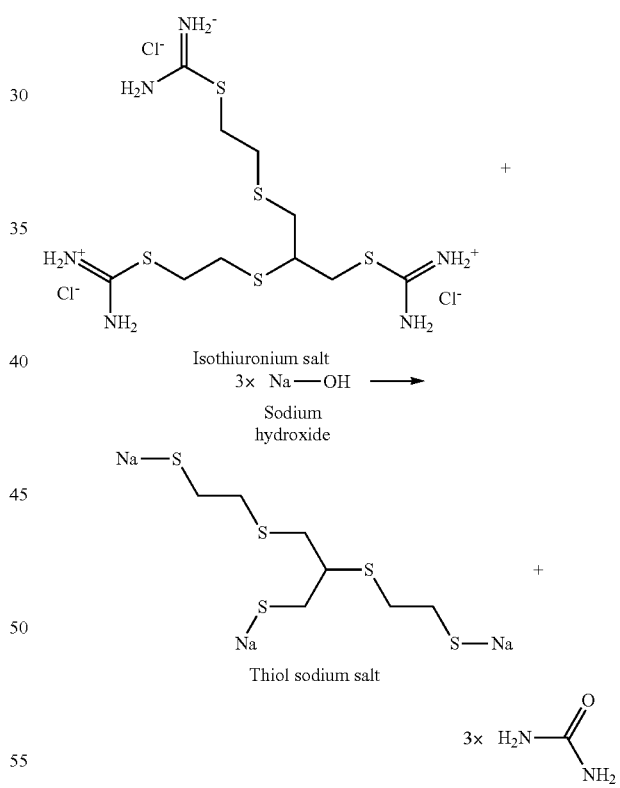

In the above reaction scheme examples 6 and 7, examples using sodium hydroxide as a base are shown, but the base used in step 4 is not limited to sodium hydroxide, and various bases can be used. The base may be an inorganic base. Examples of the inorganic base include sodium hydroxide, potassium hydroxide, and ammonia. The form of addition of the base is not limited, and the base may be added as an aqueous solution. By adding the base as an aqueous solution, the isothiuronium salt can be hydrolyzed with water contained in the aqueous solution in the presence of the base. The concentration of the base in the aqueous solution is not particularly limited, but it may be, for example, about 10 to 60% by mass. The base can be used in a ratio of, for example, 1.0 to 4.0 mol, 1.0 to 3.0 mol, or 1.2 to 2.0 mol based on 1.0 mol of the acid used in step 3. An organic solvent can be added to the reaction solution containing the isothiuronium salt after the reaction in step 3. The organic solvent can be optionally added at any stage after the reaction in step 3. The addition amount of the organic solvent may be, for example, about 0.2 to 3.0 times on a volume basis based on the amount of the reaction solution after the reaction of step 3. Examples of the organic solvent include toluene, xylene, chlorobenzene, and dichlorobenzene. In step 4, a reaction temperature may be, for example, about 10 to 80° C., and a reaction time may be, for example, about 1 to 10 hours.

<Step 5>

Next, step 5 will be described.

Step 5 is step of converting the polythiol salt obtained in step 4 into a polythiol by an acid. Thereby, one or more polythiol compounds selected from the group consisting of a polythiol compound represented by the formula (4), a polythiol compound represented by the formula (5), a polythiol compound represented by the formula (6), and a polythiol compound represented by the formula (7) can be obtained. For example, reaction scheme example 8 for converting the polythiol sodium salt shown in reaction scheme example 6 into a polythiol using hydrogen chloride (HCl) as an acid to obtain the polythiol compound represented by the formula (5) is shown below.

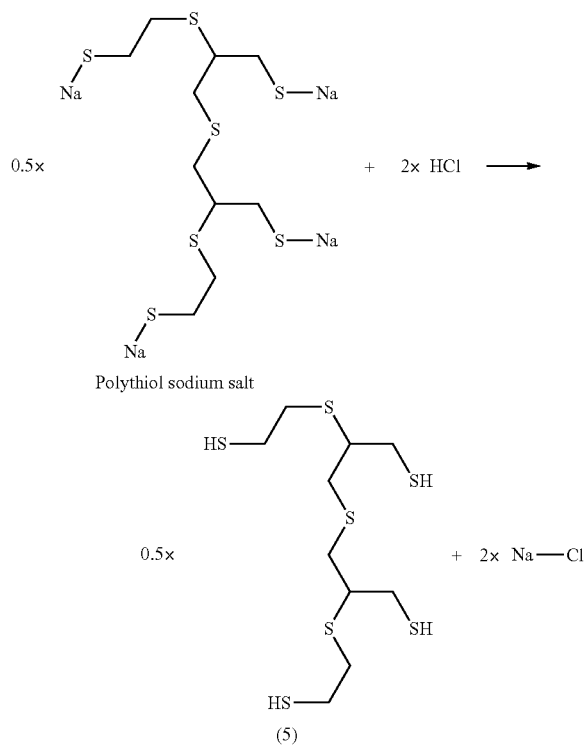

Reaction scheme example 9 for converting the polythiol sodium salt shown in reaction scheme example 6 into a polythiol using hydrogen chloride (HCl) as an acid to obtain the polythiol compound represented by the formula (4) is shown below.

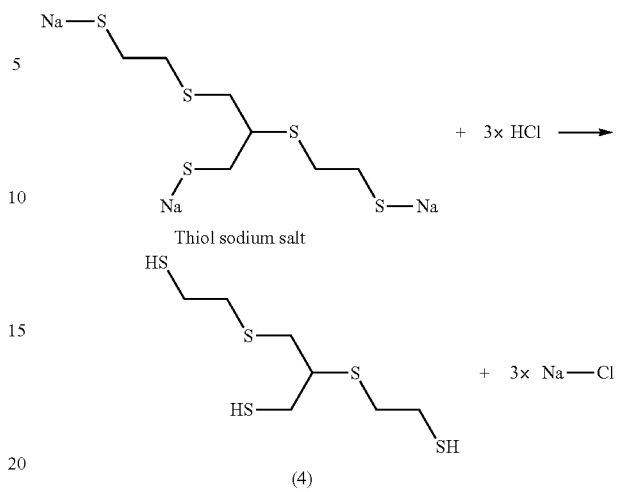

In the above reaction scheme examples 8 and 9, examples using hydrogen chloride as an acid are shown, but the acid used in step 5 is not limited to hydrogen chloride, and various inorganic acids and organic acids can be used. The details of the acid used in step 5 are as described for the acid in step 3. The polythiol salt can be converted into a polythiol by an acid in step 5 using an acid as an aqueous solution. For example, the polythiol salt can be converted into a polythiol by acid washing. Water washing may be carried out after acid washing, and water washing may be carried out while acid washing is carried out twice or more. The atmospheric temperature of an environment in which step 5 is carried out is not particularly limited, and step 5 can be carried out under an environment of, for example, an atmosphere temperature of 10 to 60° C., or 20 to 45° C. When an organic solvent is used in any of the steps, step of distilling off the organic solvent from the reaction liquid after step 5 may be carried out by a known method. Post processes such as filtration and distillation can also be carried out by known methods.

Each of the above steps can be carried out in the air, and can also be carried out under an atmosphere other than the air, for example, under a nitrogen atmosphere.

According to the steps described above, one of the polythiol compound represented by the formula (4), the polythiol compound represented by the formula (5), the polythiol compound represented by the formula (6), and the polythiol compound represented by the formula (7), or a mixture of two or more thereof can be obtained. The degree of coloration of the polythiol compound can be evaluated by, for example, the b* value prescribed in JIS Z8781-4: 2013. The b* value represents less coloration as the b* value is smaller. According to the method for producing a polythiol compound according to one aspect of the present disclosure, for example, a polythiol compound having the b* value of 2.5 or less (for example, 0.5 to 2.5) can be obtained. The method for producing a polythiol compound according to one aspect of the present disclosure uses 2-mercaptoethanol having a water content of 3000 ppm or less in step 1, whereby improvement in yield constant can also be achieved as compared with that when 2-mercaptoethanol having a water content exceeding 3000 ppm is used. When a mixture of two or more polythiol compounds is obtained, each of the polythiol compounds may be isolated by a known isolation method, or the mixture may be used as a synthetic raw material for various resins. Each of the polythiol compounds represented by the formulae (4), (5), (6), and (7) and obtained by the method for producing a polythiol compound according to one aspect of the present disclosure is a polyfunctional polythiol compound having three or four thiol groups in one molecule. In an embodiment, a cured product (polythiourethane-based resin) obtained by a curing reaction between such a polyfunctional polythiol compound and a polyiso(thio)cyanate compound can have various preferred physical properties as optical members such as a spectacle lens having a high refractive index and high heat resistance or the like.

Curable Composition and Cured Product

One aspect of the present disclosure relates to a curable composition containing the polythiol compound obtained by the above production method and the polyiso(thio)cyanate compound.

Furthermore, one aspect of the present disclosure relates to a cured product obtained by curing the curable composition.

With respect to the curable composition and the cured product, reference can be made to the descriptions relating to a method for producing a curable composition and a method for producing a cured product as described below.

Method for Producing Curable Composition

One aspect of the present disclosure relates to a method for producing a curable composition, the method including the steps of:

producing a polythiol compound by the method for producing a polythiol compound according to one aspect of the present disclosure; and mixing the produced polythiol compound with a polyiso(thio)cyanate compound to prepare the curable composition. By curing the curable composition obtained by the above production method, a polythiourethane-based resin useful as a material for an optical member such as a spectacle lens can be obtained as a cured product. Hereinafter, the production method of the curable composition will be described in more detail.

The details of the step of producing the polythiol compound are as described above for the method for producing a polythiol compound according to one aspect of the present disclosure. The curable composition can be prepared by mixing the polythiol compound thus produced with the polyiso(thio)cyanate compound. In the present disclosure and the present specification, the term "polyiso(thio)cyanate compound" is used in a sense which is inclusive of a polyisocyanate compound and a polyisothiocyanate compound. Isocyanate may be referred to as isocyanato, and isothiocyanate may be referred to as isothiocyanato. The term "iso(thio)cyanate group" is used in a sense which is inclusive of an isocyanate group (–N=C=O) and an isothiocyanate group (–N=C=S). The "polyiso(thio)cyanate compound" is a polyfunctional compound having two or more iso(thio)cyanate groups in one molecule. By the curing reaction between the polythiol compound and the polyiso(thio)cyanate compound, the thiol group of the polythiol compound can be reacted with the iso(thio)cyanate group of the polyiso(thio)cyanate compound, to obtain a reaction product having the following bond:

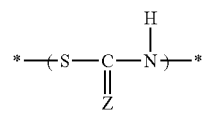

in one molecule. In the above, Z is an oxygen atom or a sulfur atom. The thiol group is reacted with the isocyanate group, whereby the above-mentioned bond in which X is an oxygen atom is formed. The thiol group is reacted with the isothiocyanate group, whereby the above-mentioned bond in which X is a sulfur atom is formed. In the present disclosure and the present specification, a reaction product (resin) containing a plurality of the above bonds in one molecule is described as "polythiourethane-based resin".

As the polyiso(thio)cyanate compound, various polyiso(thio)cyanate compounds such as an aliphatic polyiso(thio)cyanate compound, an alicyclic polyiso(thio)cyanate compound, and an aromatic polyiso(thio)cyanate compound can be used. The number of the iso(thio)cyanate groups contained in one molecule of the polyiso(thio)cyanate compound is 2 or more, and may be 2 to 4, or may be 2 or 3. Specific examples of the polyiso(thio)cyanate compounds include various compounds exemplified as the polyiso(thio)cyanate compounds in paragraph 0052 of Japanese Patent No. 5319037. Examples of the polyiso(thio)cyanate compounds include aliphatic polyisocyanate compounds such as hexamethylene diisocyanate, 1,5-pentane diisocyanate, isophorone diisocyanate, bis(isocyanatomethyl)cyclohexane, dicyclohexylmethane diisocyanate, 2,5-bis(isocyanatomethyl)-bicyclo[2.2.1]heptane, 2,6-bis(isocyanatomethyl)-bicyclo[2.2.1]heptane, bis(4-isocyanatocyclohexyl)methane, 1,3-bis(isocyanatomethyl)cyclohexane, and 1,4-bis(isocyanatomethyl)cyclohexane; and aromatic polyisocyanate compounds such as bis(isocyanatomethyl)benzene, m-xylylene diisocyanate, p-xylylene diisocyanate, 1,3-diisocyanatobenzene, tolylene diisocyanate, 2,4-diisocyanatotoluene, 2,6-diisocyanatotoluene, and 4,4'-methylenebis(phenyl isocyanate). Furthermore, halogen-substituted forms such as chlorine-substituted forms and bromine-substituted forms, alkyl-substituted forms, alkoxy-substituted forms, nitro-substituted forms, prepolymer type modified forms associated with polyhydric alcohols, carbodiimide-modified forms, urea-modified forms, biuret-modified forms, dimerized or trimerized reaction products or the like of the polyiso(thio)cyanate compound can also be used. These compounds may be used alone, or mixtures of two or more may be used.

The curable composition can be prepared by mixing the polythiol compound with the polyiso(thio)cyanate compound. The mixing ratio of the polythiol compound and the polyiso(thio)cyanate compound in the curable composition is not particularly limited. For example, the molar ratio of a thiol group contained in the polythiol compound to an iso(thio)cyanate group contained in the polyiso(thio)cyanate group may be in the range of 0.5 to 3.0, in the range of 0.6 to 2.0, or in the range of 0.8 to 1.3. The mixing ratio may be set within the above range in order to obtain a curable composition capable of providing a cured product having various excellent physical properties such as a high refractive index and high heat resistance. In one aspect, the curable composition can contain, for example, 40% by mass or more (for example, 40 to 70% by mass) of the polythiol compound based on the total amount (100% by mass) of the curable composition.

When the curable composition is prepared, one or more of other components than the polythiol compound and the polyiso(thio)cyanate compound may be mixed. Specific examples of the other components include a reaction catalyst for a curing reaction between a polythiol compound and a polyiso(thio)cyanate compound. Reference can be made to, for example, paragraphs 0055, 0057, 0058 to 0064 in Japanese Patent No. 5319037 for the other components which may be mixed. In general, it is also possible to use one or more commercially available additives as additives for various resins such as polythiourethane-based resins. The curable composition can be prepared by mixing the various components at the same time or sequentially in any order. The preparation method is not particularly limited, and any known method for preparing the curable composition can be employed without any limitation.

Method for Producing Cured Product

One aspect of the present disclosure relates to a method for producing a cured product, the method including:
step of producing a curable composition by the method for producing a curable composition according to one aspect of the present disclosure; and
curing the produced curable composition to obtain the cured product. Hereinafter, the method for producing the cured product will be described in more detail.

The details of the step of producing the curable composition are as described above for the method for producing the curable composition according to one aspect of the present disclosure. By curing the curable composition thus produced, a polythiourethane-based resin useful as a material for an optical member such as a spectacle lens can be obtained as a cured product. According to the investigation by the present inventors, it is also apparent that, by using the polythiol compound obtained by the method for producing a polythiol compound according to one aspect of the present disclosure as a synthetic raw material, a polythiourethane-based resin with reduced coloration is obtained. The degree of coloration of the resin can be evaluated based on a YI value prescribed in, for example, JIS K 7373: 2006. The YI value represents less coloration as the YI value is smaller. By using the polythiol compound obtained by the method for producing a polythiol compound according to one aspect of the present disclosure as a synthetic raw material, for example, a polythiourethane-based resin (cured product) having a YI value of less than 2.0 (for example, 1.8 or less, 0.5 to 1.8 as an example) can be obtained.

The curing reaction between the polythiol compound and the polyiso(thio)cyanate compound can be carried out by various curing treatments capable of curing the curable composition. For example, cast polymerization can be carried out for producing a cured product having a lens shape (also referred to as a "plastic lens"). In the cast polymerization, the curable composition is injected to a cavity of a molding die, in which the cavity is formed by closing a space created by two molds facing each other with predetermined space, and the polymerization reaction of the curable composition is allowed to occur within the cavity to obtain a cured product. With regard to the details of the molding die usable for the cast polymerization, reference can be made to paragraphs [0012] to [0014] of JP 2009-262480 A and FIG. 1 of the same publication. In the above-mentioned publication, the molding die in which the space between the two molds is closed with a gasket as a sealing member is shown, but a tape can also be used as the sealing member.

In one aspect, the cast polymerization can be carried out as follows. The curable composition is injected to a molding die cavity via an injection hole provided in the side surface of a molding die. After the injection, the curable composition may be polymerized (curing reaction) by heating, whereby the curable composition can be cured to obtain a cured product having an internal shape of the cavity transferred thereon. The polymerization conditions are not particularly limited, and can be appropriately set according to the composition of the curable composition or the like. As an example, the molding die having the curable composition injected to the cavity can be heated at a heating temperature of 20 to 150° C. for about 1 to 72 hours, but the conditions are not limited thereto. In the present disclosure and the present specification, the temperature such as the heating temperature or the like relating to the cast polymerization means the temperature of an atmosphere in which the molding die is placed. During the heating, the temperature can be raised at any temperature increase rate, or the temperature can be lowered (cooled) at any temperature decrease rate. After the completion of the polymerization (curing reaction), the cured product inside the cavity is released from the molding die. As it is commonly carried out for the cast polymerization, the cured product can be released from the molding die by removing the upper and lower molds forming the cavity and the gasket or tape in any order. The cured product released from the molding die can be used as a lens base material of a spectacle lens. In general, the cured product used as a lens base material of a spectacle lens can be subjected to, after release, to a post process including an annealing, a grinding process including a rounding process or the like, a polishing process, and a process for forming a coating layer such as a primer coating layer for enhancing impact resistance or a hard coating layer for increasing surface hardness. Furthermore, various functional layers such as an anti-reflection layer and a water-repellent layer can be formed on a lens base material. With regard to these processes, any known technique can be applied without any limitation. Thus, a spectacle lens in which the lens base material is the cured product can be obtained. Furthermore, by attaching the spectacle lens to the frame, a spectacle lens can be obtained.

EXAMPLES

Next, the present disclosure will be described in more detail with reference to Examples, but the present disclosure is not limited to aspects shown in Examples. Operations and evaluations described below were carried out in the air at room temperature (about 20 to 25° C.) unless otherwise specified. % and parts described below are on a mass basis unless otherwise specified.

Various physical properties in Examples were evaluated by the following method.
(1) Water Content of 2-Mercaptoethanol
In Examples and Comparative Examples, the water content of 2-mercaptoethanol used for step 1 was measured by using a Karl Fischer water content measuring apparatus (automatic moisture measuring apparatus MKC-610 model manufactured by Kyoto Electronics Co., Ltd.) under an environment of a temperature of 20 to 25° C. and an absolute humidity of 2 to 5 g/m$^3$ and a moisture vaporizing apparatus (water vaporizing apparatus ADP-611 model manufactured by Kyoto Electronics Industries Co., Ltd.). 2-mercaptoethanol used in Examples is obtained by distilling commercially available 2-mercaptoethanol and adding a molecular sieve to reduce the water content.

2-mercaptoethanol was subjected to step 1 (more specifically, mixed with a tertiary amine) within 1 hour after measuring the water content. Even though the water content of 2-mercaptoethanol does not change or changes between the measurement of the water content and step 1, the amount of change is equal to or less than the detection limit. Even though the water content of 2-mercaptoethanol does not change or changes in a normal working environment or storage environment, the amount of change is equal to or less than the detection limit.

(2) Evaluation of Coloration of Polythiol Compound (b* Value)

The b* values of the polythiol compounds obtained in Examples and Comparative Examples were measured at an optical path length of 10 mm by using a spectrophotometer U-3500 manufactured by Hitachi, Ltd.

(3) Evaluation of Coloration (YI Value) of Cured Product (Polythiourethane-Based Resin)

The YI values of cured products (0.00D, center thickness: 1.8 mm) obtained in Examples and Comparative Examples were measured by using a spectral transmittance measuring apparatus DOT-3 manufactured by Murakami Color Research Laboratory Co., Ltd.

It was confirmed by GPC (gel permeation chromatography), HPLC (high performance liquid chromatography), and MS (mass spectrometry) that intended polythiol compounds were obtained in the following Examples and Comparative Examples.

Example 1

(Step 1) 92.5 g (1.0 mol) of epichlorohydrin was added dropwise to a mixed solution of 78.1 g (1.0 mol) of 2-mercaptoethanol having a water content shown in Table 1 and 2.0 g of triethylamine over 1 hour while an internal temperature was maintained at 35 to 40° C., and the reaction solution was aged at an internal temperature of 40° C. for 1 hour. In Examples and Comparative Examples, the reaction solution was aged while the reaction solution was stirred.

(Step 2)

An aqueous solution prepared by dissolving 125.0 g (0.5 mol) of sodium sulfide nonahydrate in 100 g of pure water was added to the reaction solution after step 1 over 1 hour while an internal temperature was maintained at 40 to 45° C., and the reaction solution was further aged at an internal temperature of 5° C. for 1 hour.

(Steps 3 and 4)

303.8 g (3.0 mol) of 36% hydrochloric acid and 190.3 g (2.5 mol) of thiourea were added to the reaction solution after step 2, and the mixture was heated and stirred at an internal temperature of 110° C. for 9 hours (step 3). After the reaction solution was cooled to room temperature, 400 ml of toluene was added to the reaction solution, and 600.4 g (4.5 mol) of a 30% sodium hydroxide aqueous solution was gradually added to the reaction solution, and the reaction solution was hydrolyzed at an internal temperature of 60° C. for 4 hours (step 4).

(Step 5)

The reaction solution after step 4 was left to stand to separate the reaction solution into an aqueous layer and an organic layer, and the organic layer was then taken out. The organic layer was sequentially washed twice with 100 ml of 36% hydrochloric acid and 100 ml of water. Toluene in the organic layer after washing was distilled off with a rotary evaporator to obtain an intended polythiol compound (transparent liquid) in yield of 170.5 g (yield constant: 93.0%).

In Example 1, the reactions in steps 1 to 5 can be made to proceed as shown in reaction scheme examples 1, 2, 4, 6, and 8. In reaction scheme example 4, an isothiuronium salt having the skeleton of a polythiol compound represented by the formula (5) is shown. In reaction scheme example 6, a polythiol alkali metal salt having the same skeleton is shown, and in reaction scheme example 8, a polythiol compound represented by the formula (5) is shown. However, in step 3, as a result of the rearrangement reaction as described above, a mixture of an isothiuronium salt having the skeleton of the polythiol compound represented by the formula (5), an isothiuronium salt having the skeleton of a polythiol compound represented by the formula (6), and an isothiuronium salt having the skeleton of a polythiol compound represented by the formula (7) can be obtained. As a result, in step 5, a mixture of the polythiol compound represented by the formula (5), the polythiol compound represented by the formula (6), and the polythiol compound represented by the formula (7) can be obtained. The yield constant was calculated as yield constant=(the above yield/theoretical yield)×100 using the theoretical yield determined from the theoretical molar yield (0.5 mol) of the polythiol compounds represented by the formulae (5) to (7) obtained from the amount of 2-mercaptoethanol (1.0 mol) used in step 1. The yield constants of Examples 2 to 6 and Comparative Examples 1 and 2 were also calculated by the same method.

Example 2

An intended polythiol compound (transparent liquid) was obtained in yield of 171.1 g (yield constant: 93.3%) in the same manner as in Example 1 except that 2-mercaptoethanol having a water content shown in Table 1 was used.

Example 3

An intended polythiol compound (transparent liquid) was obtained in yield of 165.4 g (yield constant: 90.2%) in the same manner as in Example 2 except that 2.0 g of tributylamine was used as an amine used in step 1 in place of 2.0 g of trimethylamine.

Example 4

An intended polythiol compound (transparent liquid) was obtained in yield of 162.8 g (yield constant: 88.8%) in the same manner as in Example 2 except that 841.7 g of a 30% potassium hydroxide aqueous solution was used in place of 600.4 g of a 30% sodium hydroxide anqueous solution as a base used in step 4.

Example 5

An intended polythiol compound (transparent liquid) was obtained in yield of 157.0 g (yield constant: 85.6%) in the same manner as in Example 2 except that 137.0 g of epibromohydrin was used as the epihalohydrin used in step 1 in place of 92.5 g of epichlorohydrin.

Example 6

An intended polythiol compound (transparent liquid) was obtained in yield of 160.6 g (yield constant: 87.6%) in the same manner as in Example 1 except that 2-mercaptoethanol having a water content shown in Table 1 was used.

Comparative Example 1

An intended polythiol compound (yellowish transparent liquid) was obtained in yield of 138.6 g (yield constant:

75.6%) in the same manner as in Example 1 except that 2-mercaptoethanol having a water content shown in Table 1 was used.

Comparative Example 2

An intended polythiol compound was obtained in yield of 127.6 g (yield constant: 69.6%) in the same manner as in Example 1 except that 2-mercaptoethanol having a water content shown in Table 1 was used.

Example 7

(Step 1)
92.6 g (1.0 mol) of epichlorohydrin was added dropwise to a mixed solution of 78.1 g (1.0 mol) of 2-mercaptoethanol having a water content shown in Table 1 and 2.0 g of tributylamine over 1 hour while an internal temperature was maintained at 35 to 40° C., and the reaction solution was aged at an internal temperature of 40° C. for 1 hour.
(Step 2)
78.1 g (1.0 mol) of 2-mercaptoethanol having a water content and 88.8 g (1.0 mol) of a 45% sodium hydroxide aqueous solution shown in Table 1 were added dropwise to the reaction solution after step 1 over 1 hour while an internal temperature was maintained at 40 to 45° C. After the internal temperature was raised to 80° C., the reaction solution was aged for 1 hour.
(Steps 3 and 4)
303.8 g (3.0 mol) of 36% hydrochloric acid and 228.4 g (3.0 mol) of thiourea were added to the reaction solution after step 2, and the reaction solution was stirred while being heated at an internal temperature of 110° C. for 2 hours (step 3). After the reaction solution was cooled to room temperature, 200 ml of toluene was added to the reaction solution. 266.7 g (3.0 mol) of a 45% sodium hydroxide aqueous solution was gradually added to the reaction solution, and the reaction solution was hydrolyzed at 60° C. for 4 hours (step 4).
(Step 5)
The reaction solution after step 4 was left to stand to separate the reaction solution into an aqueous layer and an organic layer, and the organic layer was then taken out. The organic layer was sequentially washed twice with 100 ml of 36% hydrochloric acid and 100 ml of water. Toluene in the organic layer after washing was distilled off with a rotary evaporator to obtain an intended polythiol compound (transparent liquid) in yield of 222.4 g (yield constant: 85.4%).

In Example 7, the reactions in steps 1 to 5 can proceed as shown in reaction scheme examples 1, 3, 5, 7 and 9. The yield constant was determined as yield constant=(the above yield/theoretical yield)×100 by using the theoretical yield determined from the theoretical molar yield (1.0 mol) of the polythiol compound represented by the formula (4) obtained from the amount of 2-mercaptoethanol (1.0 mol) used in step 1. The yield constants of Example 8 and Comparative Example 3 were also calculated by the same method.

Example 8

An intended polythiol compound (transparent liquid) was obtained in yield of 214.4 g (yield constant: 82.3%) in the same manner as in Example 7 except that 2-mercaptoethanol having a water content shown in Table 1 was used.

Comparative Example 3

An intended polythiol compound (yellowish transparent liquid) was obtained in yield of 186.0 g (yield constant: 71.4%) in the same manner as in Example 7 except that 2-mercaptoethanol having a water content shown in Table 1 was used.

The b* values of the polythiol compounds obtained in Examples and Comparative Examples were measured by the method described above.

The above results are shown in Table 1. From the comparison of Examples 1 to 6 with Comparative Examples 1 and 2 and the comparison of Examples 7 and 8 with Comparative Example 3 in Table 1, it can be confirmed that, by using 2-mercaptoethanol having a water content of 3000 ppm or less in step 1, large reduction in the b* value (that is, large reduction in coloration) and large improvement in yield constant exceeding 10% are achieved.

TABLE 1

| | 2-Mercaptoethanol Water content (ppm) | Epihalohydrin used in step 1 | Alkali metal compound used in step 2 | Polythiol compound, yield constant | b* value |
|---|---|---|---|---|---|
| Example 1 | 800 | Epichlorohydrin | Sodium sulfide | 93.0% | 1.1 |
| Example 2 | 1400 | Epichlorohydrin | Sodium sulfide | 93.3% | 1.2 |
| Example 3 | 1400 | Epichlorohydrin | Sodium sulfide | 90.2% | 1.2 |
| Example 4 | 1400 | Epichlorohydrin | Sodium sulfide | 88.8% | 1.4 |
| Example 5 | 1400 | Epibromohydrin | Sodium sulfide | 85.6% | 1.8 |
| Example 6 | 2800 | Epichlorohydrin | Sodium sulfide | 87.6% | 1.5 |
| Comparative Example 1 | 3200 | Epichlorohydrin | Sodium sulfide | 75.6% | 2.6 |
| Comparative Example 2 | 10000 | Epichlorohydrin | Sodium sulfide | 69.6% | 3.6 |
| Example 7 | 800 | Epichlorohydrin | Sodium hydroxide | 85.4% | 1.3 |
| Example 8 | 2800 | Epichlorohydrin | Sodium hydroxide | 82.3% | 1.8 |
| Comparative Example 3 | 3200 | Epichlorohydrin | Sodium hydroxide | 71.4% | 3.2 |

Example 9

50.6 parts of xylylene diisocyanate, 0.01 parts of dimethyltin dichloride as a curing catalyst, 0.20 parts of acidic phosphate ester (JP-506H manufactured by Johoku Chemical Industry Co., Ltd.) as a releasing agent, and 0.5 parts of an ultraviolet absorber (Seesorb 701, manufactured by Shipro Kasei Co., Ltd.) were mixed and dissolved. Furthermore, 49.4 parts of the polythiol compound obtained in Example 1 was added and mixed to prepare a mixed solution. This mixed solution was deaerated at 200 Pa for 1 hour, and then filtered through a PTFE (polytetrafluoroethylene) filter having a pore size of 5.0 μm. The filtered mixed solution (curable composition) was injected to a molding die for a lens having a diameter of 75 mm and including a glass mold of −4.00 D or 0.00 D and a tape. The molding die was charged into an electric furnace, gradually heated from 15° C. to 120° C. over 20 hours, and kept for 2 hours for polymerization (curing reaction). After the completion of the polymerization, the molding die was removed from the electric furnace, and released to obtain a cured product (plastic lens). The obtained plastic lens was further subjected to annealing for 3 hours in an annealing furnace having a furnace temperature of 120° C.

Comparative Example 4

A plastic lens was prepared in the same manner as in Example 9 except that a polythiol compound was changed to the polythiol compound obtained in Comparative Example 1.

Example 10

52.0 parts of xylylene diisocyanate, 0.05 parts of dimethyl tin dilaurate as a curing catalyst, 0.20 parts of acidic phosphate ester (JP-506H manufactured by Johoku Chemical Industry Co., Ltd.) as a releasing agent, and 0.5 parts of an ultraviolet absorber (Seesorb 701, manufactured by Shipro Kasei Co., Ltd.) were mixed and dissolved. Furthermore, 48.0 parts of the polythiol compound obtained in Example 7 was added and mixed to prepare a mixed solution. This mixed solution was deaerated at 200 Pa for 1 hour, and then filtered through a PTFE (polytetrafluoroethylene) filter having a pore size of 5.0 μm. The filtered mixed solution (curable composition) was injected to a molding die for a lens having a diameter of 75 mm and including a glass mold of −4.00 D or 0.00 D and a tape. This molding die was charged into an electric furnace, gradually heated from 30° C. to 120° C. over 20 hours, and kept for 2 hours for polymerization (curing reaction). After the completion of the polymerization, the molding die was removed from the electric furnace, and released to obtain a cured product (plastic lens). The obtained plastic lens was further subjected to annealing for 3 hours in an annealing furnace having a furnace temperature of 120° C.

Comparative Example 5

A plastic lens was prepared in the same manner as in Example 10 except that a polythiol compound was changed to the polythiol compound obtained in Comparative Example 3.

The YI values of the plastic lenses obtained in Examples and Comparative Examples were measured by the method described above.

The above results are shown in Table 2. From the comparison of Example 9 with Comparative Example 4 and the comparison of Example 10 with Comparative Example 5, it can be confirmed that, by using the polythiol compound obtained by using 2-mercaptoethanol having a water content of 3000 ppm or less as a synthetic raw material, large reduction in the YI value (that is, large reduction in coloration) is achieved.

TABLE 2

| | Examples and Comparative Examples in which polythiol compounds are obtained | YI value |
|---|---|---|
| Example 9 | Example 1 | 1.7 |
| Comparative Example 4 | Comparative Example 1 | 2.0 |

TABLE 2-continued

| | Examples and Comparative Examples in which polythiol compounds are obtained | YI value |
|---|---|---|
| Example 10 | Example 7 | 1.8 |
| Comparative Example 5 | Comparative Example 3 | 2.2 |

Finally, the above-mentioned respective aspects are summarized.

According to one aspect, there can be provided a method for producing a polythiol compound, the method including: step 1 of reacting 2-mercaptoethanol having a water content of 3000 ppm or less on a mass basis, with epihalohydrin to obtain a halide represented by the formula (1); step 2 of reacting the halide represented by the formula (1) with an alkali metal compound selected from the group consisting of an alkali metal sulfide and an alkali metal hydroxide to obtain a polyol compound selected from the group consisting of a polyol compound represented by the formula (2) and a polyol compound represented by the formula (3); step 3 of reacting the polyol compound with thiourea in the presence of an acid to obtain an isothiuronium salt; step 4 of hydrolyzing the isothiuronium salt in the presence of a base to obtain a polythiol salt; and step 5 of converting the polythiol salt into a polythiol by an acid to obtain at least one polythiol compound selected from the group consisting of a polythiol compound represented by the formula (4), a polythiol compound represented by the formula (5), a polythiol compound represented by the formula (6), and a polythiol compound represented by the formula (7).

According to the above-mentioned method for producing a polythiol compound, a polythiol compound with reduced coloration can be provided in high yield constant.

In one aspect, the alkali metal compound is an alkali metal compound selected from the group consisting of sodium sulfide and sodium hydroxide.

In one aspect, the polythiol salt is a salt selected from the group consisting of a polythiol alkali metal salt and a polythiol ammonium salt.

According to another aspect, there is also provided a method for producing a curable composition, the method including: step of producing a polythiol compound according to the production method; and step of mixing the produced polythiol compound with a polyiso(thio)cyanate compound to prepare the curable composition.

According to the method for producing a curable composition, the curable composition capable of providing a cured product with reduced coloration can be obtained.

According to another aspect, there is also provided a method for producing a cured product, the method including: step of producing a curable composition according to the production method; and step of curing the produced curable composition to obtain the cured product.

According to the method for producing a cured product, a cured product with reduced coloration can be provided.

In one aspect, the curing step is carried out by subjecting the curable composition to cast polymerization.

In one aspect, the cured product is a spectacle lens base material.

It should be considered that the embodiments disclosed herein are exemplary in all respects and are not restrictive. The scope of the present disclosure is defined by the claims, rather than by the description above, and the scope is intended to include meanings equivalent to claims and all changes within the scope.

One aspect of the present disclosure is useful in the field of producing various optical members such as a spectacle lens.

What is claimed is:

1. A method for producing a polythiol compound, the method comprising:

reacting 2-mercaptoethanol having a water content of 3000 ppm or less on a mass basis, with epihalohydrin to obtain a halide represented by the formula (1),

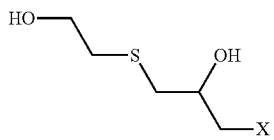

Formula (1)

wherein X represents a halogen atom;

reacting the halide represented by the formula (1) with an alkali metal compound selected from the group consisting of an alkali metal sulfide and an alkali metal hydroxide to obtain a polyol compound selected from the group consisting of a polyol compound represented by the formula (2) and a polyol compound represented by the formula (3),

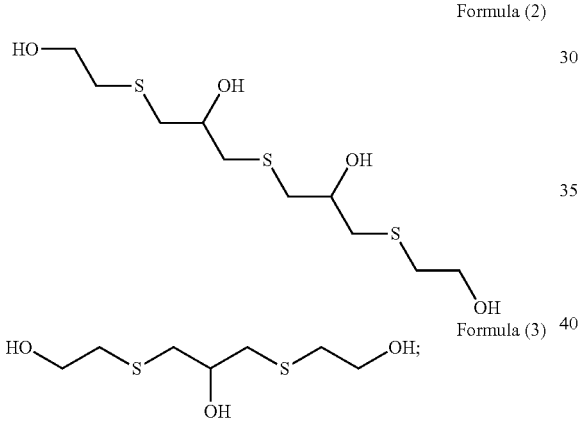

Formula (2)

Formula (3)

reacting the polyol compound with thiourea in the presence of an acid to obtain an isothiuronium salt;

hydrolyzing the isothiuronium salt in the presence of a base to obtain a polythiol salt; and converting the polythiol salt into a polythiol by an acid to obtain at least one polythiol compound selected from the group consisting of a polythiol compound represented by the formula (4), a polythiol compound represented by the formula (5), a polythiol compound represented by the formula (6), and a polythiol compound represented by the formula (7),

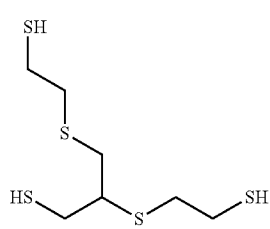

Formula (4)

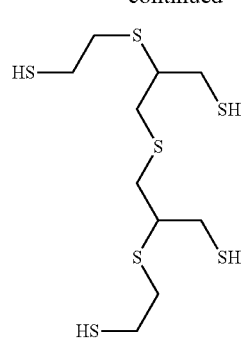

Formula (5)

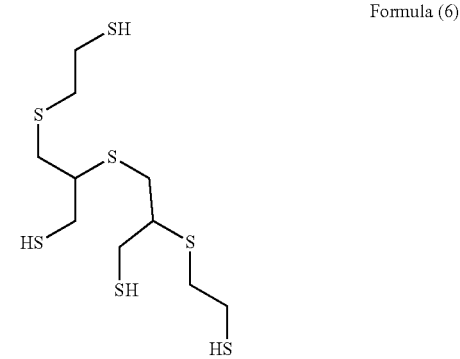

Formula (6)

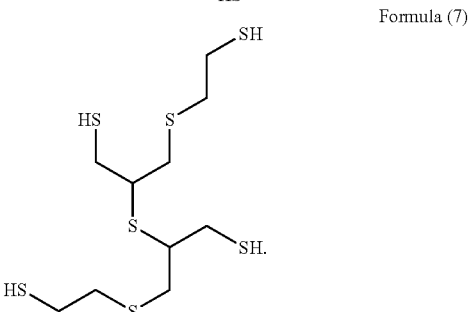

Formula (7)

2. The method for producing a polythiol compound according to claim 1,
wherein the alkali metal compound is an alkali metal compound selected from the group consisting of sodium sulfide and sodium hydroxide.

3. The method for producing a polythiol compound according to claim 1,
wherein the polythiol salt is a salt selected from the group consisting of a polythiol alkali metal salt and a polythiol ammonium salt.

4. A method for producing a curable composition, the method comprising:
producing a polythiol compound according to the production method according to claim 1; and
mixing the produced polythiol compound with a polyiso(thio)cyanate compound to prepare the curable composition.

5. A method for producing a cured product, the method comprising:
producing a curable composition according to the production method according to claim 4; and
curing the produced curable composition to obtain the cured product.

6. The method for producing a cured product according to claim 5, wherein the curing is carried out by subjecting the curable composition to cast polymerization.

7. The method for producing a cured product according to claim 5, wherein the cured product is a spectacle lens base material.

8. A method for producing a curable composition, the method comprising:
producing a polythiol compound according to the production method according to claim 2; and
mixing the produced polythiol compound with a polyiso(thio)cyanate compound to prepare the curable composition.

9. A method for producing a curable composition, the method comprising:
producing a polythiol compound according to the production method according to claim 3; and
mixing the produced polythiol compound with a polyiso(thio)cyanate compound to prepare the curable composition.

10. A method for producing a cured product, the method comprising:
producing a curable composition according to the production method according to claim 8; and
curing the produced curable composition to obtain the cured product.

11. A method for producing a cured product, the method comprising:
producing a curable composition according to the production method according to claim 9; and
curing the produced curable composition to obtain the cured product.

12. The method for producing a cured product according to claim 10,
wherein the curing is carried out by subjecting the curable composition to cast polymerization.

13. The method for producing a cured product according to claim 11,
wherein the curing is carried out by subjecting the curable composition to cast polymerization.

14. The method for producing a cured product according to claim 10,
wherein the cured product is a spectacle lens base material.

15. The method for producing a cured product according to claim 11,
wherein the cured product is a spectacle lens base material.

16. The method for producing a polythiol compound according to claim 1,
wherein the reacting of the 2-mercaptoethanol having a water content of 3000 ppm or less on a mass basis with the epihalohydrin is performed in the absence of a solvent or in the presence of a solvent consisting of an alcohol.

* * * * *